(12) United States Patent
Wimmer et al.

(10) Patent No.: US 11,045,494 B2
(45) Date of Patent: Jun. 29, 2021

(54) USE OF POTASSIUM HYDROXIDE IN THE TREATMENT OF ACTINIC KERATOSIS

(71) Applicant: Infectopharm Arzneimittel und Consilium GmbH, Heppenheim (DE)

(72) Inventors: Thomas Wimmer, Frankfurt am Main (DE); Bertil Wachall, Hemsbach (DE); Philip Zoeller, Darmstadt (DE); Alessandro Giunta, Rome (IT)

(73) Assignee: Infectopharm Arzneimittel und Consilium GmbH, Heppenheim (DE)

( * ) Notice: Subject to any disclaimer, the term of this patent is extended or adjusted under 35 U.S.C. 154(b) by 0 days.

(21) Appl. No.: 15/736,514

(22) PCT Filed: Jul. 10, 2015

(86) PCT No.: PCT/EP2015/065840
§ 371 (c)(1),
(2) Date: Dec. 14, 2017

(87) PCT Pub. No.: WO2017/008831
PCT Pub. Date: Jan. 19, 2017

(65) Prior Publication Data
US 2018/0185409 A1  Jul. 5, 2018

(51) Int. Cl.
*A61K 33/00* (2006.01)
*A61K 45/06* (2006.01)
*A61P 17/12* (2006.01)
*A61P 17/02* (2006.01)
*A61K 9/00* (2006.01)

(52) U.S. Cl.
CPC ............ *A61K 33/00* (2013.01); *A61K 9/0014* (2013.01); *A61K 45/06* (2013.01); *A61P 17/02* (2018.01); *A61P 17/12* (2018.01); *A61K 2300/00* (2013.01)

(58) Field of Classification Search
CPC .................................. A61K 33/00; A61P 17/12
See application file for complete search history.

(56) References Cited

U.S. PATENT DOCUMENTS

| 5,310,419 | A  | * | 5/1994  | McCoy ............... A61K 33/02 |
|-----------|----|---|---------|---------------------------------|
|           |    |   |         | 106/1.05                        |
| 7,205,003 | B2 |   | 4/2007  | Maibach et al.                  |
| 8,569,320 | B2 |   | 10/2013 | Melzer et al.                   |
| 2003/0034322 | A1 | * | 2/2003 | Doherty ............ B65D 41/0478 |
|           |    |   |         | 215/228                         |
| 2004/0242507 | A1 |   | 12/2004 | Bymose et al.                  |
| 2007/0142317 | A1 | * | 6/2007 | Warren ............... A61K 9/0014 |
|           |    |   |         | 514/46                          |
| 2013/0197089 | A1 |   | 8/2013 | Warnecke                        |
| 2015/0110924 | A1 |   | 4/2015 | Bromley                         |

FOREIGN PATENT DOCUMENTS

| EP | 2 471 541   | A1 |   | 7/2012  |
|----|-------------|----|---|---------|
| EP | 2 620 146   | A1 |   | 7/2013  |
| EP | 2 860 130   | A1 |   | 4/2015  |
| EP | 2 785 336   | B1 |   | 9/2015  |
| JP | 5315404     | A  | * | 12/1978 |
| RU | 2146919     | C1 |   | 3/2000  |
| RU | 2201236     | C2 |   | 3/2003  |
| UA | 81222       | C2 |   | 12/2007 |
| UA | 56321       | U  |   | 1/2011  |
| WO | 01/24699    | A2 |   | 4/2001  |
| WO | 03/026680   | A2 |   | 4/2003  |
| WO | 2008/043386 | A1 |   | 4/2008  |
| WO | 2008/057282 | A1 |   | 5/2008  |
| WO | 2011/126539 | A2 |   | 10/2011 |
| WO | 2013/079211 | A1 |   | 6/2013  |

OTHER PUBLICATIONS

"Performing In-Office KOH Prep Tests", Consultant, Sep. 2013, vol. 12, Issue 9, printed from https://www.consultant360.com/articles/performing-office-koh-prep-tests on Jan. 2, 2018.*
Belisario J C: "Recent advances in topical cytotoxic therapy of skin cancer and precancer", Elsevier Science Publishers & V.C.N. Blight, 1972, pp. 349-365. (Abstract).
International Search Report of PCT/EP2015/065840, dated Feb. 19, 2016.
William J. McIntyre et al: "Treatment Options for Actinic Keratoses", American Family Physician, vol. 76, No. 5, 2007, pp. 667-671, XP002667626 (URL: http://www.aafp.org/afp/2007/0901/9667.htm).
A.N. Khlebnikova et al., Morphology of Actinic Keratosis (Морфологические особенности актинического кератоза), Russian Journal of Skin and Venereal Diseases (Российский журнал кожных и венерических болезней), 2012, No. 2, pp. 10-14.
"Handbook of Pharmaceutical Excipients Fifth Edition", Pharmaceutical Press and American Pharmacists Association, 2006, pp. 605-606.

(Continued)

*Primary Examiner* — Gina C Justice
(74) *Attorney, Agent, or Firm* — Collard & Roe, P.C.

(57) ABSTRACT

An agent in the form of potassium hydroxide (KOH) in a pharmaceutically acceptable composition is used in the dermal treatment of actinic keratosis. The composition may be an aqueous alkaline solution of potassium hydroxide and topically applied to the skin or on the scalp, within the face, the neck, the nose, as well as on the bosom.

9 Claims, No Drawings

(56) References Cited

OTHER PUBLICATIONS

Mashkovsky M.D., "Medicinal Remedies (Manual for Practitioners) Part 2 Twelfth Edition", 1993, pp. 450-455, Moscow "Meditsina", (with statement of relevance).

Lawrence et al., "A comparison of the efficacy and safety of Jessner's solution and 35% trichloroacetic acid vs 5% fluorouracil in the treatment of widespread facial actinic keratoses.", Abstract, JAMA Dermatology, 1995, 1 page.

Wikipedia article "Precancerous condition", https://en.wikipedia.org/wiki/Precancerous_condition, downloaded Apr. 23, 2020, 3 pages.

\* cited by examiner

USE OF POTASSIUM HYDROXIDE IN THE TREATMENT OF ACTINIC KERATOSIS

CROSS REFERENCE TO RELATED APPLICATIONS

This application is the National Stage of PCT/EP2015/065840 filed on Jul. 10, 2015, the disclosure of which is incorporated by reference. The international application under PCT article 21(2) was published in English.

TECHNICAL FIELD

The present invention relates to an agent of potassium hydroxide (KOH), specifically in a pharmaceutically acceptable composition, especially compositions in the form of or comprising an aqueous solution of potassium hydroxide (KOH), as the active ingredient, for the therapeutic, especially topical dermal use in the treatment of actinic keratosis.

BACKGROUND

Actinic keratosis is a condition of damage of the upper cornea layer induced by light, especially sun light (UV-radiation). Typical symptoms are scaly, or crusty patches of skin especially of the skin of the face, the forehead, the neck, the hands and the nose. Usually the damage progresses slowly, however after a longer period of time it can also turn into a specific kind of cell carcinoma, the so called squamous cell carcinoma. In general actinic keratosis is known as a hyper proliferative condition of the skin material related to an increased cell growth.

Most frequently actinic keratosis occurs on areas of white fair skinned people having less pigmented skin especially in the age of 50 years and more, who are often exposed to sun light either because of their working area or due to increased outdoor activities. A general summary of common treatment methods of actinic keratosis is published by WILLIAM J. MCINTYRE ET AL: "Treatment Options for Actinic Keratoses", American Family Physician, vol. 76, no. 5 2007, pages 667-671, XP002667-626, (URL:http://www.aafp.org/afp/2007/0901/p667.html). As can be seen, there are different methods of treatment such as surgical (ablative) methods (cryosurgery, electrotherapy, photodynamic therapy using 5-aminolevulinic acid) as well as topical dermal treatments. Topical treatments include the use of creams, gels or ointments comprising active agents such as fluorouracil, diclophenac, imiquimod, or hyaluronic acid in combination with the aforementioned active ingredients. However such treatments may lead to crusty or scaly skin areas.

STATE OF THE ART

WO 2011/126539 A2 is related to the use of extracts of *Hamelia patens* extract in the treatment of various skin disorders for example actinic keratosis.

EP 2 079 525 A1 discloses the use of deuterium dioxide in the treatment of conditions related to hyper proliferative disorders such as several keratoses. In one embodiment patches or bandages, creams or gels are used. Thereby the increased skin cell proliferation shall be reduced. It is assumed that deuterium oxide inhibits the mitotic cell cycle (cell division) and that hyper proliferative cells collect more deuterium oxide than normal proliferative cells.

EP 2 620 146 A1 suggests the use of ibuprofen in the topical (dermal) treatment of actinic keratosis. Suitable compositions are creams, gels or ointments.

WO 2013/079211 (EP 2 785 336) is related to the use of polyoxylated long chain fatty alcohols (macrogols) such as polidocanol ($C_{12}$ (7-11) polyethoxylated dodecanol). Suitable application forms are creams, gels, micro emulsions, trans dermal application forms or epicutaneous injections. The amount of the active ingredient (polidocanol) is depending on the mode of application (topical-dermal or trans dermal or injection) and may be in the range of up to 30 g. An in vivo activity has not been shown.

In view of the period of effectiveness of an active ingredient when used topically or in a dermal mode it should at first be considered to apply a pharmaceutical active agent without incurrence of undesired side effects. Furthermore, in this connection a selective application of the active ingredient to the desired area to be treated is important as well.

Moreover, systemic actions being possible by the aforementioned application forms such as trans dermal-diffusive deliverance or by injections and/or local excess of dosage may not be favorable.

In addition an accumulation of the active ingredient in the skin area to be treated should be avoided.

OBJECT OF THE INVENTION

The object of the present invention is the provision of an agent and an easily produced composition, respectively useful in the local treatment of actinic keratosis whereby a systemic accumulation of the active ingredient or a direct accumulation of the active agent in the skin area to be treated may essentially be avoided. On the other hand the use of such an agent or composition should cause a considerable, especially rapid healing reaction thereby allowing a repeated application. In addition the avoidance of serious side effects related to the active ingredient in the skin area to be treated were favorable.

Solution of the Object

The above object/s is/are solved by the provision and use of an agent of potassium hydroxide (KOH), specifically in a pharmaceutically acceptable composition, and to compositions, respectively comprising or specifically consisting of an aqueous solution comprising potassium hydroxide (KOH), preferably as the main active agent, in an indication related suitable amount of e.g. of about from 0.01 up to 15 wt. %, especially of from 0.1 up to 10 wt. % and most favorably in an amount of from 0.1 up to 5 wt. %, each related to the total amount (wt. %) of the composition.

Such pharmaceutically acceptable KOH and such pharmaceutically acceptable solutions comprising potassium hydroxide (KOH) are known in the art and may easily be prepared, respectively by admixture of water and potassium hydroxide or by dilution of a pre-prepared commercially available solution. Such solutions are alkaline, preferably exhibiting a pH value of between 8 and 15, more preferably of 9.5 to 15 and most preferred of 13 to 15.

The active agent and the composition, respectively, comprising the same may be applied by spraying, droping, spreading onto the area to be treated.

Preferably the area to be treated is selected from the skin, especially the skin of/on the scalp, head, the skin within the face, the neck, the nose, the skin of the hands and arms/forearms as well as on the decoltée, and combinations thereof.

Optionally further additives may be incorporated into the composition used according to the invention, e.g. in an amount/concentration of from 0.01 to 5 wt. %, related to the total amount of the composition (wt. %).

Such further additives may be selected from the group comprising surface active agents such as non ionic surfactants, especially those having a HLB-value of from 9 to 20 having O/W properties. Such surfactants are $C_1$-$C_{15}$-alkyl-$C_{8-22}$-fatty alcohol ethers or $C_1$-$C_{15}$-alkyl-$C_{12-22}$-fatty acid esters, or (poly)oxylated-$C_{8-22}$-fatty alcohols and (poly) oxylated $C_{8-22}$-fatty acid esters, especially $C_{10}$-$C_{18}$-fatty alcohols or (poly)ethoxylated and/or (poly)-propoxylated derivatives thereof (=fatty alcohol ethoxylates and/or -propoxylates) having a degree of ethoxylation (EO) and/or propoxylation (PO), respectively of 8-25, or mixtures thereof. Specific representatives of such compounds are e.g. laureth (9) (hydroxypoly-ethoxydodecane=macrogollaurylether (9)) or polyoxyethylated cetyl and/or stearylether such as polyoxyethylated (20) or (25) cetylstearylether (Ceteareth (20) or (25)) or polyoxyethylen(10) or 820) cetylether (Ceteth(10) or (20)) or polyoxyethyled (10) stearylether (Steareth (10)), or polyoxyethyled (10) oleylether (Oleth(10)).

Further examples of non ionic surfactants are non ionic glucosides such as esters and ethers of glucose, methyl glucose or saccharose and saturated and/or partially unsaturated $C_{12-22}$-fatty acids or $C_{8-22}$-fatty alcohols, polyoxyethylated and/or polyoxypropylated sugar esters or sugar ethers of $C_{12}$-$C_{18}$ fatty acids and $C_{12}$-$C_{18}$ fatty alcohols having an EO- and PO- degree, respectively of 8-25.

Surfactants may be present in an amount of from 0.01 to 3 wt. %, preferably from 0.1 to 2 wt. %, especially of from 0.5 to 1.8 wt. %, related to the total amount of the composition.

In a specific embodiment the agent or composition according to the invention may further comprise as additive/s 0.1 to 2 wt. % of one or more non ionic surfactants having an HLB (hydrophilic-lipophilic balance) value of 12-18, especially $C_{10}$-$C_{18}$-fatty alcohols or (poly)ethoxylated and/or -(poly)-propoxylated derivatives thereof as described above.

Further optional additives may be selected from preservatives such as alcohols, or macro-molecular additives such as geling agents, or salts, especially to assure the pharmacological properties of the solution comprising potassium hydroxide, in relation to its concentration.

In general such additives are not necessary and preferably not be comprised by the pharmaceutically acceptable agent and compositions of potassium hydroxide (KOH), especially the respective aqueous composition used according to the present invention.

Especially, in specific cases geling agents such as hydroxyl propyl cellulose or polyacrylates are not necessary within the agent/composition used according to the present invention and are therefore preferably not comprised therein when no geling agent is desired.

In a preferred embodiment an aqueous solution comprising potassium hydroxide, especially consisting of water and potassium hydroxide, in an amount of 3 to 7 wt. %, especially 5 wt. % KOH, related to the total amount of the composition, and preferably comprising no further additives, is used according to the invention in the treatment of actinic keratosis.

In another preferred embodiment an aqueous solution comprising potassium hydroxide, especially comprising potassium hydroxide in an amount of 3 to 7 wt. %, preferably 5 wt. %, as well as 0.1 to 2 wt. %, each related to the total amount of the composition, of one or more non ionic surfactants having an HLB value of 12 to 18 is used according to the invention in the treatment of actinic keratosis.

The agent/composition of and used, respectively according to the invention comprises potassium hydroxide (KOH) as the pharmaceutically active ingredient, preferably as the sole (main) active ingredient in the desired amount and water (aqueous solution). Further known active agents related to the same indication (actinic keratosis) such as ibuprofen, fluorouracil, diclophenac, deuterium dioxide, imiquimod (4-Amino-1-isobutyl-1H-imidazo[4,5-c]chinolin), hamelia (patens) extract, or other keratinolytically active agents such as vitamin-A-acid or salicylic acid and/or the pharmaceutically acceptable derivatives thereof or combinations thereof or with aforementioned agents may be included in the compositions of and used according to the invention if necessary or desired for any reason. Such further known active ingredients, especially as mentioned above, however are usually not necessary and the present agent/aqueous compositions with potassium hydroxide (KOH) according to the invention do preferably not comprise such further active agents.

Specifically the agent/composition as used according to the invention is preferably free of further agents being active in regard to actinic keratosis, selected from the group consisting of diclophenac, deuterium dioxide, fluorouracil, imiquimod, Hamelia (patens)—extract or combinations thereof or therewith.

On the other hand it is possible to omit higher amounts e.g. more than 3 wt. %, of polyoxylated fatty alcohols specifically such as pegylated (7-11-polyethylenglykol)-$C_{12-16}$-fatty alcohol ethers (macrogols) such as polyoxy (ethoxylated) (9)-$C_{12}$-fatty alcohol (hydroxypolyethoxy (7-11)-dodecane) in amounts possibly being pharmaceutically active in relation to actinic keratosis.

The compositions/agent of and used according to the present invention may however comprise lower amounts thereof (polyoxylated fatty alcohols as described above), e.g. up to 2.5 wt. % (e.g. 0.1 to 2 wt. %, or 1 to 1.8 wt. %) in relation to the total amount of the composition.

The present invention is also related to the application of an agent or more preferably to a composition consisting of potassium hydroxide (KOH) and water, especially water purified for pharmaceutical application, wherein potassium hydroxide is present in an amount of from 0.1 to 10 wt. %, preferably 0.5 to 5 wt. %, especially in an amount of 5 wt. %.

The composition/agent may be applied onto the skin area by delivering the same from a suitable application bottle which may reversibly be opened/closed, especially in connection with suitable application means such as swab, spatula, or others. It is also possible to use dosage or spray devices or other application forms known to the man skilled in the art.

The composition or agent of or used according to the invention may be used in the form of a pharmaceutical or a medical product.

A medical product according to the invention means a product, composition or device comprising such compositions or products, the main activity thereof in or on the human body neither being provided by pharmacological or immunological means nor by metabolic action, however the action thereof may be supported thereby.

A pharmaceutical agent and a pharmaceutically active agent/composition, respectively according to the invention especially means substances or compositions of substances or devices comprising such substances/compositions determined for the use in or on the human body in order to act on or correct the physiological functions by a pharmacological, immunological or metabolic action.

In order to apply the composition/agent according to the invention it may be comprised in an application product, especially in a medical or pharmaceutical product, preferably consisting of an aqueous solution comprising potassium hydroxide (KOH), specifically in an amount of from 0.1 to 10 wt. %, more preferably 0.5 to 5 wet. %, and most preferred in an amount of 5 wt. % as the active ingredient, in the treatment of actinic keratosis, together with an applicator device for specific (dermal) application of the (fluid) aqueous composition to the skin of the human body in need thereof whereby the application device comprises a container comprising the fluid composition/agent exhibiting a reversible cap and a suitable outlet enabling the deliverance of the fluid composition/agent.

Mode/Kind of Application

In accordance with the present invention the agent or composition as indicated is applied to the skin area in need of a treatment by dropping, spraying, spreading using a suitable applicator device such as a painting. The amount of the active agent needed is depending on the size, color, deepness of the lesion/skin damage and may optionally be determined by a skilled man and/or a physician. The application dosage may vary from e.g. 0.1. to 10 drops or from 0.01 to 0.5 ml/application rate. Consequently about some square millimeters to some square centimeters of the lesions of the skin area to be treated will be covered. Thereby an improvement of the condition is achieved in a surprisingly rapid mode.

As patients mammals, especially humans in a condition of need of a treatment as described herein are eligible. The composition as used according to the invention are preferably related to human beings.

According to the invention the skin area exhibiting actinic keratosis is obviously stimulated for rapid reaction. Without being bound to a specified theory it may be assumed that the initial irritation based on the alkaline milieu initiates a physical abrasive removal of the plaques, bumps or maculae thereby helping improving the normalization of cell proliferation of the skin cells affected.

Within the sense of the present invention actinic keratosis means a hyper proliferative condition or disease of non- but potentially premalignant kind, which however under certain conditions may progress into a malignant state. The treatment of actinic keratosis is consequently recommended and important in order to avoid such malignancy and metastasis and therefore may be a suitable means of the prevention thereof. The above disease is in contrast to other skin disorders such as inflammatory diseases like dermatitis, psoriasis or sun burn, which may be related to an acidosis which is not the case in a keratosis related condition. It was therefore highly surprising that such non-acidic conditions may be treated using an alkaline agent or solution without the occurrence of serious side effects.

Preparation of the Agents/Compositions

Pharmaceutically acceptable KOH and pharmaceutically acceptable solutions comprising potassium hydroxide (KOH) and a carrier are known in the art and may easily be prepared, respectively by admixture of water which then is the carrier and potassium hydroxide or by dilution of a pre-prepared commercially available solution. Such solutions are alkaline, preferably exhibiting a pH value of between 8 and 15, more preferably of 9.5 to 15 and most preferred of 13 to 15. As far as desired one or more additives as aforementioned may be added under agitation. The resulting fluid may then be filled into suitable containers as known in the art.

EXAMPLES

The invention is further illustrated by the following non-limiting examples.

Example 1: Preparation of a KOH Composition 1

A composition for use according to the invention is prepared by solving 5 g of potassium hydroxide PH. Eur. in 100 ml water (purified for pharmaceutical purposes) in a manner known per se. The solution is subsequently filled into a suitable container. A sterile filling is not necessary because of the high alkaline pH value of 14.

Example 2: Preparation of a KOH Composition 2

A composition for use according to the invention is prepared by solving 3 g of potassium hydroxide PH. Eur. in 100 ml water (purified for pharmaceutical purposes) in a manner known per se. Subsequently 0.6 wt. %, related to the total amount of the composition, of Ceteareth(25) is added under agitation. Then the clear fluid solution is filled into a suitable container. A sterile filling is not necessary because of the high alkaline pH value of 13.5.

Example 3: Application of a Composition According to the Invention 34 patients (21 male, 13 female, mean age about 68) affected by actinic keratosis did apply twice a day during a period of 15 days a composition according to example 1 by spreading it in an amount sufficient to cover the respective skin area in the face and in some cases on the body as well. If necessary the application was repeated.

After 15 days, 1 month and 12 weeks, respectively the lesions were evaluated by dermoscopy and compared to the initial situation.

Results:

79.4% of the patients showed a complete resolution of the target treated lesion, 35.3% after the first treatment cycle and 44.1% after 2 cycles. None of the treated lesions showed recurrence. No serious side effects were observed.

The invention claimed is:

1. A method for dermal treatment of actinic keratosis, the method comprising:
preparing a composition consisting of an aqueous solution of potassium hydroxide (KOH), wherein the aqueous solution is alkaline and has a pH value of between 9.5 and 15, wherein the aqueous solution consists of water and the potassium hydroxide, and wherein the potassium hydroxide is in an amount of 5 wt. %, related to the total amount of the water; and
applying the composition dermally to a patient.

2. The method according to claim 1 wherein the aqueous solution has a pH value of between 12 and 15.

3. The method according to claim 1, wherein the composition is applied topically to skin of the patient, on a scalp of the patient, within a face, neck, nose, hands, arms, or forearms of the patient, or on the decollete of the patient, and combinations thereof.

4. The method according to claim 1, further comprising a step of preparing the composition by admixing water and potassium hydroxide.

5. The method according to claim 1, further comprising a step of preparing the composition by diluting a pre-prepared commercially available solution.

6. The method according to claim 1, wherein the application of the composition dermally to the patient occurs via an applicator device.

7. The method according to claim 6, wherein the applicator device comprises a container having a reversible cap and an outlet, the container initially holding the composition.

8. The method according to claim 1, wherein the composition is applied topically by spraying, spreading, or draping the composition onto the skin area to be treated.

9. The method according to claim 1, wherein the pH value of the aqueous solution is between 13 and 15.

* * * * *